United States Patent [19]

Metzger et al.

[11] Patent Number: 4,930,521
[45] Date of Patent: Jun. 5, 1990

[54] VARIABLE STIFFNESS ESOPHAGEAL CATHETER

[76] Inventors: William T. Metzger, 1760 Cass Ct., Libertyville, Ill. 60048; Hossein Jadvar, c/o Medical Computer Laboratory University of Michigan, 4421 EECS Bldg., Ann Arbor, Mich. 48109-2122

[21] Appl. No.: 324,919

[22] Filed: Mar. 17, 1989

[51] Int. Cl.⁵ .............................................. A61N 1/00
[52] U.S. Cl. ................................... 128/786; 128/772; 128/419 P
[58] Field of Search ............... 128/784, 785, 786, 642, 128/419 P, 772; 604/164, 280

[56] References Cited

U.S. PATENT DOCUMENTS

| | | | |
|---|---|---|---|
| 3,804,098 | 4/1974 | Friedman | 128/786 |
| 4,355,646 | 10/1982 | Kallok et al. | 128/786 |
| 4,699,157 | 10/1987 | Shonk | 128/786 |
| 4,706,688 | 11/1987 | Michael et al. | 128/785 |

OTHER PUBLICATIONS

An article entitled "Transesophageal Electrocardiography and Cardiac Pacing: State of the Art", published in the journal Circulation in 1987.

Primary Examiner—Lee S. Cohen
Assistant Examiner—Scott Getzow

[57] ABSTRACT

A transesophageal pacing catheter has an elongated body portion with a proximal end and a distal end. The distal end carries first and second spaced-apart pacing electrodes thereon. The distal end terminates in a closed, rounded, flexible polyethylene tip. The body portion of the catheter is formed with inner and outer elongated cylindrical, polyethylene members. Electrical connections for the spaced-apart electrodes extend through the body portion between the two polyethylene cylindrical members to the proximal end thereof. At the proximal end the electrical conductors terminate at first and second conductive connecting members. A removable stylet slidably engages a central cavity of the body portion and provides a variable degree of flexibility thereto.

14 Claims, 2 Drawing Sheets

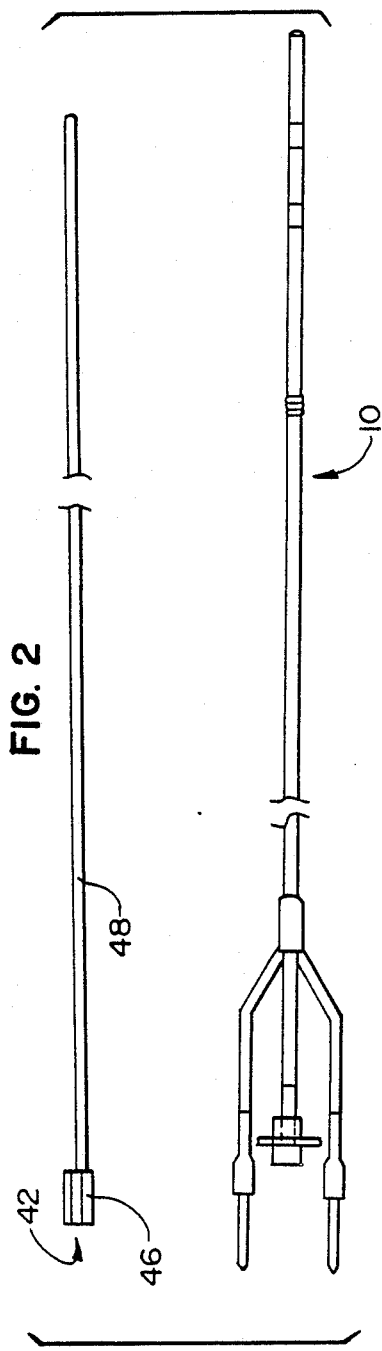
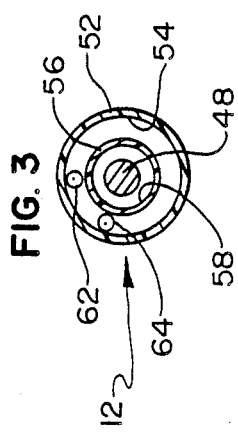
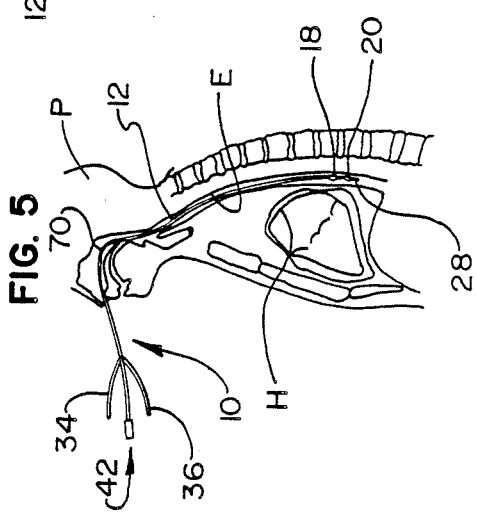

4,930,521

VARIABLE STIFFNESS ESOPHAGEAL CATHETER

FIELD OF THE INVENTION

The invention pertains to devices usable for non-invasive heart pacing. More particularly, the invention pertains to esophageal catheters usable for noninvasive cardiac pacing.

BACKGROUND OF THE INVENTION

Transvenous catheters are known for use in invasive cardiac pacing. Such catheters have a distal end which can be inserted, via a vein of a patient, into the appropriate chamber of a patient's heart so as to carry out a pacing operation.

It's also been known to use transvenous catheters, at least experimentally, in esophageal pacing. Such catheters have first and second spaced-apart electrodes located on a distal end thereof. The electrodes are positioned in the esophagus appropriately with respect to the posterior surface of the patient's heart so as to carry out a pacing operation. Results of experiments using such bipolar transvenous catheters for esophageal pacing were presented, in part, at the Fifty-Third Scientific Sessions of the American Heart Association, Nov. 19, 1980. Results of that work were subsequently published in the journal *Circulation* in 1982.

Notwithstanding the above-noted uses for transvenous catheters, none of the known transvenous catheters provide any adjustment of the flexibility or stiffness thereof during insertion. Further, transvenous catheters at times terminate in a hard electrode member which can cause some discomfort to the patient on insertion through the nasal passages into the esophagus.

Hence, there continues to be a need for costeffective esophageal pacing catheters which are readily inserted and which cause minimal patient discomfort and/or trauma.

SUMMARY OF THE INVENTION

A variable stiffness esophageal catheter has an elongated body portion with a proximal end and a distal end. The catheter has a soft tip which is rounded and sealed which is carried on the distal end of the body portion.

A stylet is slidably positioned within the body portion and is usable for adjusting the stiffness characteristic thereof. First and second electrodes are carried spaced apart from one another on the distal end of the body portion. One of the electrodes is positioned adjacent the flexible tip. The electrodes can be formed of platinum.

In a disclosed embodiment the body portion in formed out of first and second elongated flexible polyethylene cylindrical members. One member is positioned inside of the other member and extends axially therewith.

First and second conducting wires extend axially in a region between the two cylindrical polyethylene members from the proximal end of the body portion to the distal end thereof. The conducting wires are each electrically connected to a respective one of two electrodes at the distal end of the catheter. At the proximal end of the catheter the two electrical wires are each terminated in an electrical connector.

The stylet extends axially through the interior elongated polyethylene member. The stylet is formed of a stainless steel rod. The flexibility of this rod is much less than that of the catheter body.

The catheter may be inserted into a patient's esophagus via the nasal passages and sinus cavities. alternately, the catheter could be inserted orally. The soft, flexible tip reduces trauma to the patient's tissues and improves insertion comfort.

The slidably removable stylet can be used to alter the flexibility of the body portion as the catheter is being positioned in the esophagus of the patient.

Once the spaced-apart electrodes are properly located with respect to the posterior surface of the patient's heart, the electrical connections at the proximal end may be used to apply electrical energy to the spaced-apart electrodes to carry out a pacing procedure.

Alternately, the electrodes can be used to carry out a cardiac monitoring function.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 2 is a top view of the esophageal catheter with the stylet completely withdrawn therefrom;

FIG. 3 is a view in section taken along plane 3—3 of FIG. 1;

FIG. 4 is a view in section taken along plane 4—4 of FIG. 1; and

FIG. 5 is a fragmentary left sagittal view of a patient with an esophageal catheter inserted and properly positioned adjacent a posterior heart surface.

DETAILED DESCRIPTION OF THE PREFERRED EMBODIMENTS

Figure 1:
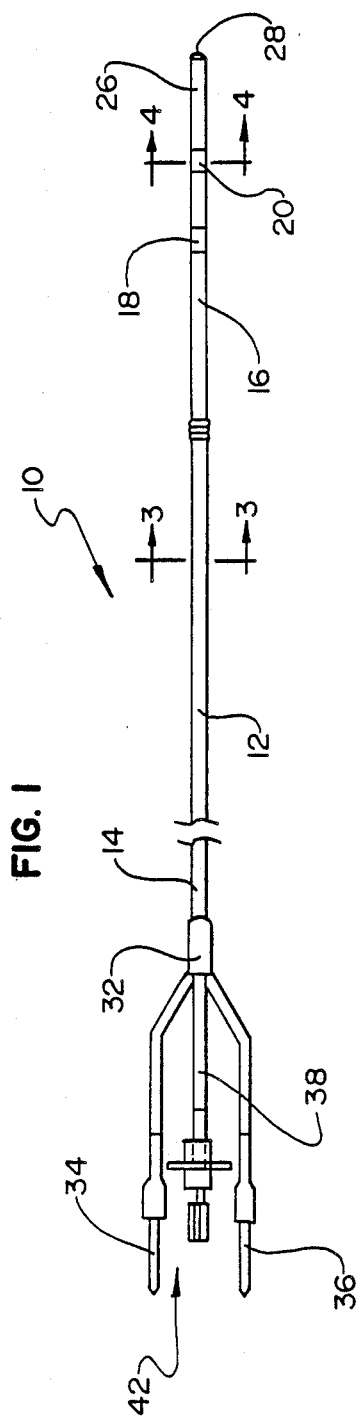
FIG. 1 is a top view of an esophageal catheter with the stylet partly withdrawn therefrom.

While this invention is susceptible of embodiment in many different forms, there is shown in the drawings and will be described herein detail a specific embodiment thereof with the understanding that the present disclosure is to be considered as an exemplification of the principles of the invention and is not intended to limit the invention to the specific embodiment illustrated.

A variable flexibility esophageal catheter 10 is illustrated in FIG. 1. The catheter 10 includes a flexible elongated body portion 12 with a proximal end 14 and a distal end 16.

Carried on the body portion 12 adjacent the distal end 16 are first and second spaced-apart electrodes 18 and 20. Adjacent the electrode 20 is a soft catheter tip 26 which has a rounded and sealed end 28.

The body portion 12 and the catheter tip 26 can both be formed of polyethylene. The tip 26 is flexible.

The proximal end 14 terminates at a bifurcated coupler 32. Input to the bifurcated coupler 32 includes a first electrical connector lead 34 which is electrically coupled through the coupler 32 and the body member 12 to the electrode 20. A second electrical connector lead 36 is coupled via the coupler 32 and the body member 12 to the electrode member 18.

A centrally located lumen 38 to the coupler 32 slidably receives an elongated axially extending stylet 42.

The stylet 42 is illustrated at FIG. 1 partly withdrawn from the body portion 12 of the catheter 10.

The slidably engageable stylet 42 provides for variable flexibility as the catheter 10 is being inserted via a patient's nasal passages into the esophagus. The soft round-ended catheter tip 26 improves insertion comfort and reduces trauma to the patient's tissues.

FIG. 2 illustrates the catheter 10 with the stylet 42 removed therefrom. The stylet 42 includes a manually grippable knob 46 coupled to an elongated cylindrical stiffening member 48.

The member 48 can be formed of a medical-grade stainless steel and may be somewhat flexible. However, the degree of flexibility of the member 48 is substantially less than the degree of flexibility of the body member 12 with the stylet 42 withdrawn.

FIG. 3, a sectional view taken along plane 3—3 of FIG. 1, illustrates the structure of the body member 12 in detail. The body member 12 is formed of an exterior flexible cylindrical member 52. The member 52 defines an interior, closed, axially extending region or lumen 54.

Positioned within the axially extending lumen 54 is a second flexible elongated cylindrical member 56. The member 56 defines a second, closed, interior elongated lumen 58 therein.

The member 54 is formed of polyethylene. The member 56 is formed of flexible, high-density polyethylene.

First and second insulated conducting wires 62 and 64 are positioned in the lumen 54. The wires 62 and 64 extend substantially axially through the length of the body member 12 and respectively couple the proximal end electrical connector leads 34 and 36 to the electrodes 20 and 16 respectively.

The insulated wires 62, 64 can be formed as a twisted pair or can be located coextensively in the region 54 without being twisted together.

The elongated body portion 48 of the stylet 42 is illustrated in FIG. 3 positioned in the second axially extending elongated lumen 58.

FIG. 4, a sectional view taken along plane 4-4 of FIG. 1, illustrates the relationship of the electrode 20 to the body member 12. The electrode 20 is carried on the polyethylene member 52 in contact therewith. Since the stylet 42 has been illustrated in FIG. 1 partly withdrawn from the body member 12, it does not appear in the section of FIG. 4.

The electrodes 18, 20 can be formed of platinum or any other acceptable conductor. The electrodes 18, 20 could be deposited on the member 52. Alternately, the electrodes 18, 20 may be formed as separate conducting members that are then affixed to the distal end of the member 52. The exact way in which the electrodes 18, 20 are formed and attached to the body member 12 is not a limitation of the present invention.

FIG. 5 illustrates a fragmentary sagittal view of a patient P. The patient P has an esophagus E in which a catheter 10 in accordance with the present invention has been inserted. The electrodes 18 and 20 have been positioned adjacent a posterior surface of the heart H of the patient P.

As illustrated in FIG. 5, the body portion 12 of the catheter 10 has been inserted through the nasal passages of the patient P. Proper insertion has required that the body portion 10 undergo a substantial bend 70, on the order of ninety degrees, when passing from the region of the patient's sinuses into the esophagus E. The soft tip 28 minimizes trauma as the distal end 16 makes the bend 70.

The catheter 10 can be inserted with the stylet 42 positioned therein. The stylet 42 is of a size which is flexible enough to readily deflect or bend as necessary to pass into the esophagus.

When the electrodes 18 and 20 has been positioned far enough into the esophagus, the stylet 42 can be withdrawn and the patient can, by swallowing, cause the electrodes 18, 20 and the soft tip 28 to move downwardly into the esophagus E until the electrodes approach the desired position adjacent the posterior surface of the heart H. Alternately, the stylet 42 can be left fully inserted into the catheter 10 until the electrodes 18 and 20 have been properly positioned.

As illustrated in FIG. 5, the soft tip 28 is particularly useful in reducing trauma to the patient P during insertion of the catheter.

The exterior diameter of the cylindrical polyethylene member 52 can be on the order of 0.058 inches. The interior diameter thereof can be on the order of 0.045 inches. The exterior diameter of the member 52 corresponds to the size of a 4 French catheter.

The exterior diameter of the high-density polyethylene cylindrical member 56 can be on the order of 0.030 inches. The interior diameter of the member 56 can be on the order of 0.022 inches. The exterior diameter of the body 48 of the stylet can be on the order of 0.016 inches. The overall length of the catheter 10 can be on the order of 1 meter.

It will be understood that the actual diameter of the member 52 is not a limitation of the present invention. For example, alternate sizes such as 5 or 6 French could also be used.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A variable stiffness esophageal catheter insertable into the esophagus of a subject via the nasal passages comprising:

an elongated, flexible body portion having a proximal end and a distal end;

a soft flexible tip carried on said distal end of said body portion; and means for adjusting a stiffness characteristic of said body portion with said catheter deflectable in an angle on the order of ninety degrees and with said soft flexible tip minimizing trauma to adjacent nasal tissues.

2. An esophageal catheter as in claim 1 including a first electrode carried on said body portion adjacent said flexible tip.

3. An esophageal catheter as in claim 2 with said body portion defining an elongated, axially extending cylindrical region therein.

4. An esophageal catheter as in claim 3 including an elongated stylet slidably received, at least in part, within said cylindrical region.

5. An esophageal catheter as in claim 2 including a second electrode carried on said body portion spaced from said first electrode.

6. An esophageal catheter as in claim 1 with said body portion including:

a first elongated flexible cylindrical member defining a first axially extending region therein; and a second elongated flexible cylindrical member defining a second axially extending region therein with said second member positioned within said first member in said first axially extending region 7. An esophageal catheter as in claim 6 including a conductive electrode carried on said first cylindrical member adjacent said flexible tip.

8. An esophageal catheter as in claim 7 including a flexible elongated conducting member carried by said body portion within said first axially extending region with a first end coupled to said electrode and with a second end located adjacent said proximal end.

9. An esophageal catheter as in claim 6 with said adjusting means including an elongated, cylindrical stiffening member sliding received in said second region.

10. An esophageal catheter of varying flexibility which can be comfortably inserted into the esophagus of a subject via that subject's nasal passages comprising:

an elongated, cylindrical flexible body portion, said body portion having a proximal end and a distal end and including a first elongated flexible cylindrical member defining an axially extending region therein.

a second elongated flexible cylindrical member defining a second axially extending region therein with said second member positioned within said first member in said axially extending region;

an elongated, removable cylindrical stiffening member slidably received within said second region;

a soft, flexible, non-conducting tip carried on said distal end, said tip having a rounded and sealed insertion end; and at least a first cylindrical conducting member carried on said body portion adjacent said distal end displaced from said soft tip.

11. An esophageal catheter as in claim 10 with said tip formed of polyethylene.

12. An esophageal catheter as in claim 11 including a second cylindrical conducting member carried on said body member adjacent said first conducting member and spaced therefrom.

13. An esophageal catheter as in claim 12 including first and second conductive wires carried within said body portion and extending from said distal end to said proximal end with each of said wires coupled to a respective one of said conducting members.

14. An esophageal pacing catheter which is easily and comfortably insertable into the esophagus of a subject via the nasal passages comprising:

a soft cylindrical flexible, polyethylene tip with a closed, curved end region;

an elongated flexible, cylindrical polyethylene body member with a proximal end and a distal end, said tip affixed to said distal end at a region displaced from said curved end, said body member defining an internal, axially extending lumen therein;

first and second pacing electrodes carried on said body member adjacent said distal end and spaced from one another;

first and second elongated conductive wires carried within said body member and extending substantially axially therein, each said wire having a proximal end and a distal end and with a said distal end of each said wire electrically coupled to a respective one of said electrodes; and an elongated, cylindrical metal member with a distal end slidably received within said axially extending lumen including a manually manipulatable proximal end for withdrawing said cylindrical metal member, thereby altering a stiffness characteristic of the catheter with said soft flexible tip minimizing trauma to the subject while said body member is being slidably inserted into the esophagus via the nasal passages of the subject and during deflation thereof while passing from the nasal passages into the esophagus.

* * * * *

UNITED STATES PATENT AND TRADEMARK OFFICE
CERTIFICATE OF CORRECTION

PATENT NO. : 4,930,521

DATED : June 5, 1990

INVENTOR(S) : William T. Metzger et al.

It is certified that error appears in the above-identified patent and that said Letters Patent is hereby corrected as shown below:

On the face of the patent: item [73] should be inserted to read as follows:

Assignee: Arzco Medical Electronics, Inc., Vernon Hills, IL

Signed and Sealed this

Twenty-first Day of January, 1992

Attest:

HARRY F. MANBECK, JR.

*Attesting Officer*     *Commissioner of Patents and Trademarks*